United States Patent [19]

Procenko

[11] 4,378,126
[45] Mar. 29, 1983

[54] CONTACT LENS INSERTION APPARATUS

[76] Inventor: Leonid Procenko, 2346 Westwood Blvd., Ste. 4, Los Angeles, Calif. 90064

[21] Appl. No.: 207,218

[22] Filed: Nov. 17, 1980

[51] Int. Cl.³ .............................................. A61F 9/00
[52] U.S. Cl. ................................................ 294/1 CA
[58] Field of Search .................. 294/1 CA, 25, 64 R; 128/303 R; 206/5.1; 351/160

[56] References Cited

U.S. PATENT DOCUMENTS

| 2,287,576 | 6/1942 | Solomon | 294/64 R |
| 3,008,748 | 11/1961 | Rives | 294/64 R |
| 3,139,298 | 6/1964 | Grabiel | 294/1 CA |
| 3,177,874 | 4/1965 | Spriggs | 294/25 X |
| 3,600,028 | 8/1971 | Henning | 294/1 CA |
| 4,026,591 | 5/1977 | Cleaveland | 294/1 CA |
| 4,093,291 | 6/1978 | Schurgin | 294/1 CA |
| 4,201,408 | 5/1980 | Tressel | 294/1 CA |

FOREIGN PATENT DOCUMENTS 1395355  3/1965  France ............................. 294/1 CA Primary Examiner—Johnny D. Cherry
Attorney, Agent, or Firm—Romney, Golant, Martin, Disner & Ashen

[57] ABSTRACT

A contact lens insertion apparatus incorporating an illuminated target for guiding the lens into the proper position on the cornea of an eye. The lens is held in place on the apparatus by a flexible cup that maintains a vacuum between itself and the lens. A suction breaking assembly enables easy removal of the lens from the apparatus once the lens has been properly positioned on the cornea. Also included is a lower eyelid opener which not only lowers the lid for easy insertion of the lens but also provides a pivot arm enabling the user to swing the applicator up, and easily and correctly position the lens on the eye.

5 Claims, 3 Drawing Figures

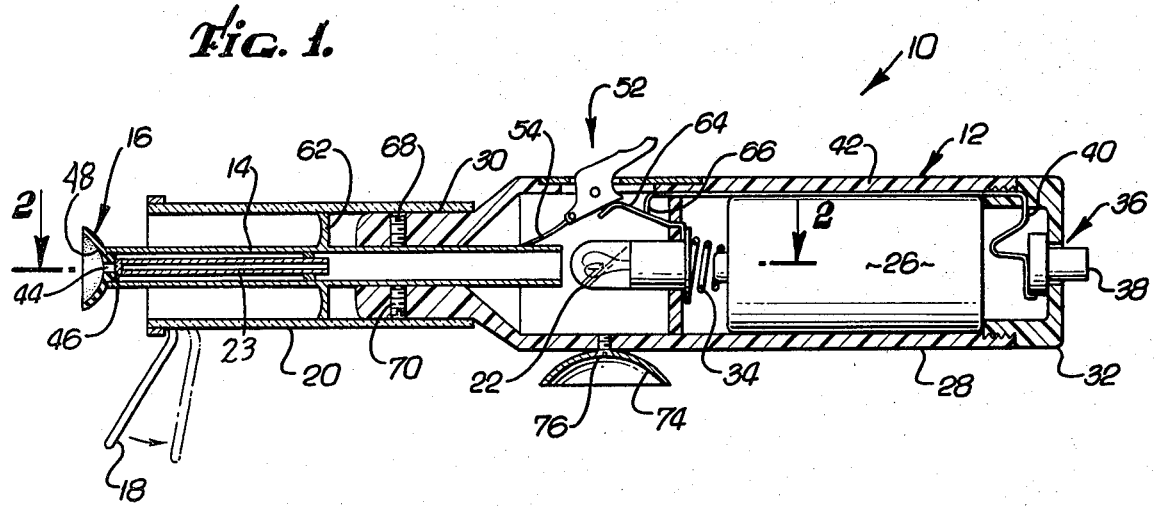
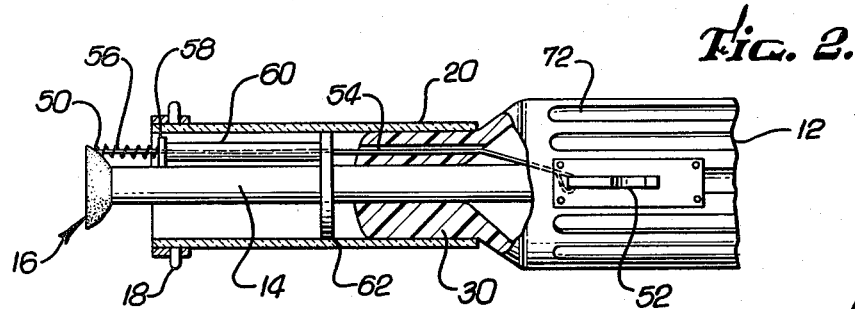
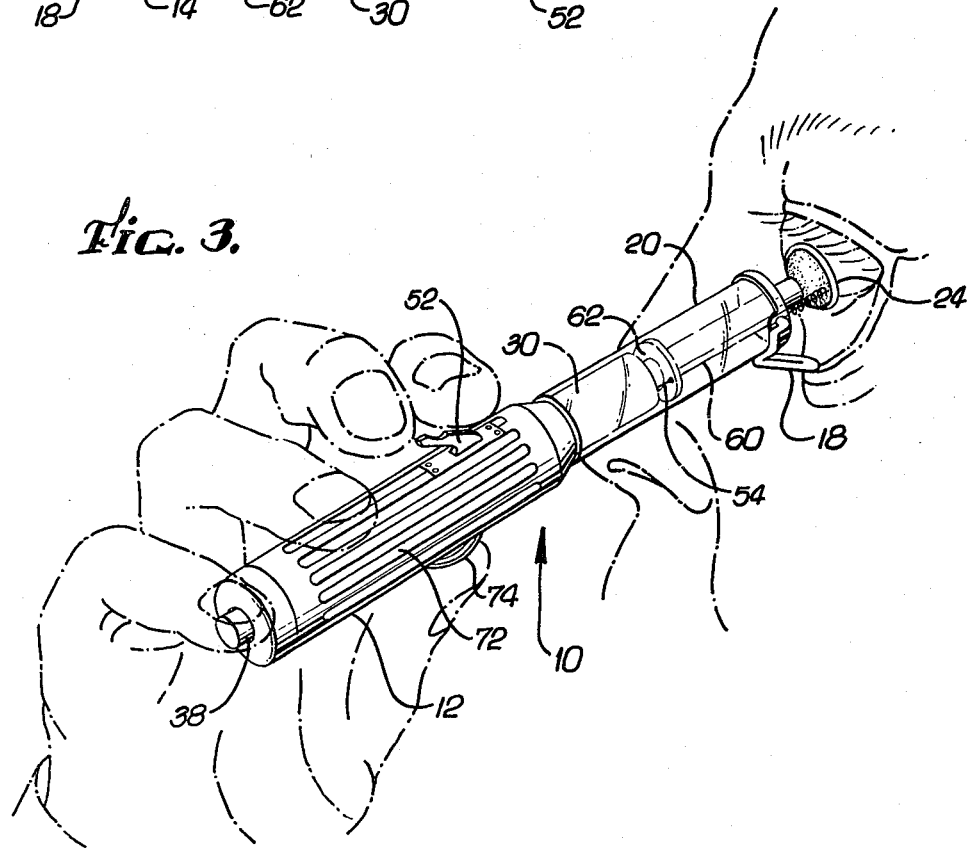

CONTACT LENS INSERTION APPARATUS

BACKGROUND

1. Field of the Invention

The present invention relates to a contact lens insertion apparatus and, in particular, to an improved contact lens insertion apparatus that can be operated easily by anyone, even persons whose muscular control and coordination render it difficult or impossible to insert contact lenses.

2. Prior Art

A variety of contact lens insertion devices utilizing a light source have been designed. Most of these have included a flash light type housing with a lens holder positioned at the top of the housing. A lens may be maintained in the holder in one of a variety of ways, including fluid surface tension, as described in U.S. Pat. No. 3,743,337 to Crary, or suction, as described in U.S. Pat. No. 3,304,113 to Hutchison.

U.S. Pat. No. 3,139,298 to Grabiel teaches a device for inserting contact lenses wherein the lens is retained in a lens holder only by the force of gravity. Thus if the device is tipped to one side or the other the lens will fall off. U.S. Pat. Nos. 3,600,028 to Henning; 3,791,689 to Boone, et al.; 3,934,914 to Carruthers, and the above-identified patent to Hutchison all include means for creating a vacuum to hold a lens in position on a lens holder. Hutchison includes a bulb connected to the holder through pneumatic tubing. The bulb is squeezed and released in order to provide suction or pressure as needed to keep the lens in place or to release the lens. Boone, et al., and Carruthers teach a resiliant pouch surrounding a light path and communicating with a lens holder by way of a hole in the bottom of the lens holder. By squeezing the pouch, a partial vacuum may be created or released for operating the lens holder. Henning teaches another vacuum type arrangement wherein a tube can be pulled upward to create the partial vacuum and pushed downward to release the vacuum. U.S. Pat. No. 4,201,408 to Tressel teaches a similar method of creating a partial vacuum to hold the lens in place. An actuating member may be squeezed to evacuate air from a tube in communication with the lens holder. Tressel also teaches an end piece which can be placed against the cheek of the operator in order to steady the device.

All of the patents utilizing a partial vacuum to hold the lens in position suffer from a common ailment. The lens holder includes a passageway leading to the bulb, pouch, etc. When the suction is created foreign matter may be, and frequently is, drawn into the passageway. This is an especially difficult area to clean, thus providing an environment for the growth of bacteria. In addition, when these devices release the lens, a small burst of air from the bulb, pouch, etc. thrusts some of this foreign matter onto the lens and into the eye of the operator. The net effect of the air passage leading to the lens holder renders these devices less than sanitary.

U.S. Pat. No. 4,093,291 to Shurgin teaches a lens inserter that uses liquid adhesion to hold the lens to the inserter. Shurgin's device also contains a pair of tongs for grasping the side of the lens for removal thereof from the eye.

While most of these designs use illumination to facilitate the proper positioning of the lens on the eye, various methods are used to accomplish the illumination. In particular, the light element may be contained in the housing, as in the Crary and Hutchison patents, or an external light source may be used whereby the illumination is conducted to the lens through either an optical fiber, as in the Boone, et al. patent, or a light pipe, as in the Carruthers patent. Both of these methods provide an illuminated target facilitating the guidance of the lens into the proper position on the eye.

Some of these devices are easier to use than others. Some are in fact quite cumbersome. By way of example, none of the designs provides any means for opening the eyelid while steadying the device for persons who have difficulty holding either their hands or head steady. In addition, the means for providing suction to hold the lens in place frequently requires manipulation of a separate element, such as the squeeze bulb taught by Hutchison. This manipulation may be quite difficult for older people or those having less than full operation of their hands.

SUMMARY OF THE INVENTION

The present invention solves the problems that now exist by providing an apparatus for inserting contact lenses comprising a lens holder extension tube attached to a housing for providing a light channel; and a lens holder attached to the lens holder extension tube for holding a contact lens to be inserted by forming a partial vacuum between the lens and the lens holder, the lens holder including means at its center communicating with the light channel provided by the lens holder extension tube for allowing light to pass therethrough and thereby assisting the operator in guiding a lens. The invention also includes illuminating means contained within the housing and positioned at the end of the extension tube for providing illumination to the lens holder; a power source for powering the illuminating means; an eyelid opener extending from the housing for opening the lower eyelid of the eye, for steadying the applicator against the cheek bone of the user, and for guiding the lens into the proper position on the eye by pivoting the apparatus above the eyelid opener to bring the lens to the eye; a suction breaker operationally connected to the lens holder for allowing air to enter between the lens and the lens holder in order to break the suction of air therebetween and thereby easily remove the apparatus from the lens once the lens has been positioned on the eye; and a thumb holder attached to the housing in a position approximately 180° displaced from a suction breaker switch for facilitating the gripping of the apparatus by an individual and for facilitating the proper alignment of the individual's fingers upon the apparatus for easy operation thereof.

Accordingly it is an object of the present invention to provide an improved contact lens insertion apparatus that is extremely easy to use.

Another object of the present invention is to provide an improved contact lens insertion device that can be used, even in the dark, by people having extremely impaired eyesight.

A further aim of the present invention is to provide an improved contact lens insertion device that can be used by people having an unsteady hand and/or head.

It is an additional aspect of the present invention to provide an improved contact lens insertion device that contains a simple, yet reliable, suction and suction breaking mechanism for holding the lens in place on the applicator and for releasing the lens after contact has been made with the eye of the operator.

A further object of the present invention is to provide an improved contact lens insertion device that maintains the lens in position by a partial vacuum, without containing an air passage leading to the lens holder, thusly avoiding the collection of unsanitary or harmful foreign matter within the device.

Yet another aspect of the present invention is to provide an improved contact lens insertion device that contains an eyelid opener greatly facilitating the insertion of the contact lens onto the cornea of the eye.

It is a further aim of the present invention to provide an improved contact lens insertion device that includes a thumb holder for facilitating the gripping of the applicator by the operator and insuring that the operator's hand is properly positioned to facilitate simple one-handed operation of the apparatus.

Another object of the present invention is to provide an improved contact lens insertion device that is reliable, simply constructed, and inexpensive to manufacture.

The foregoing objects, advantages, features and results of the present invention together with various other objects, advantages, features and results thereof which will be evident to those skilled in the art in light of this disclosure may be achieved with the exemplary embodiments of the invention described in detail hereinafter and illustrated in the accompanying drawings.

BRIEF DESCRIPTION OF THE DRAWINGS

FIG. 1 is a side sectional view of the applicator showing the interrelationship of the various components.

FIG. 2 is a partial plan cut away view showing the positioning of the suction release mechanism.

FIG. 3 is a perspective view showing the insertion apparatus in use.

DESCRIPTION OF THE PREFERRED EMBODIMENTS

While the present invention is susceptible of various modifications and alternative constructions, an embodiment is shown in the drawings and will herein be described in detail. It should be understood however that it is not the intention to limit the invention to the particular forms disclosed; but, on the contrary, the intention is to cover all modifications, equivalences and alternative constructions falling within the spirit and scope of the invention as expressed in the appended claims.

Users of contact lenses frequently encounter difficulty inserting the lens into position on their eye. Balancing the lens on a finger tip, the standard method of applying contact lenses, may prove impossible for an individual with an unsteady hand. Furthermore, the user may lack the requisite hand-eye coordination to properly place the lens on his eye with his finger. In addition, even normal eyes cannot focus on an object within one or two inches of the eye itself. Clearly the individual requiring corrective lenses frequently has greater difficulty in focusing on small and close objects than the person with normal vision. And, in special cases, like those involving people who have had the natural lens removed, in what is commonly called a cataract operation, vision is permanently and substantially impaired making it impossible to focus at all.

Lens insertion devices usually attempt to solve the problems associated with inserting contact lenses by providing both a member to support the lens and a light to guide its insertion. The light is generally channeled from below the support member through the optical axis of the lens. This light is easily sighted as the lens is moved toward the eye. The channeled light provides a thin ray that can be seen when it is aligned coaxially with the optical axis of the eye. The correct position for an inserted lens is on the cornea of the eye with the optical axis of the lens coincident with the optical axis of the eye. By aligning the light with the optical axis of the eye the lens is automatically placed in the correct position for insertion.

The present invention provides an improvement to the prior art contact lens insertion devices described hereinabove. Referring now to FIG. 1, a contact lens insertion apparatus 10 is shown including a housing 12, an extension tube 14 and a lens holder 16. The apparatus also includes an eyelid opener 18 which may be attached either to the housing or to a sleeve 20.

The apparatus contains its own light source 22 to channel light through the extension tube 14. A light focusing tube 23 is positioned within the extension tube to narrow the beam of light to a pencil thin ray. The channeled light extends along the axis of the tube through the optical axis of a lens 24 shown in FIG. 3. This line of light greatly facilitates the alignment of the lens with the eye. In particular, it allows the user to be sure that he is inserting the lens to the proper position on his eye. The self contained light source is superior to the light pipes used in some of the prior art devices. The light pipes frequently required the operator to stare into a lamp. Thus, the channeled light was not easily differentiated from the background light. Although the optical fiber relieved the operator from staring at the lamp, it still required the availability of a light in the room. On the other hand, the present invention can be used in rooms with no light, or even in a darkened room. The self-contained light source may be a bulb 22, as shown in FIG. 1, or any other light generating means.

The applicator includes a power source for the light. This avoids the inconvenience and difficulty associated with the power cord that otherwise would be necessary. The structure to achieve this is simple, reliable and inexpensive. The housing 12 contains the power source such as a battery 26 positioned in the usually suitable manner. The housing itself may be metal or high-impact plastic or any other suitable material strong enough to house the elements described herein and be handled by an operator in the manner shown in FIG. 3.

The housing comprises a handle portion 28 and a neck portion 30. The handle portion contains a removable cap 32 at its end. The cap threadably engages the interior surface of the housing to detachably connect therewith. This detachable connection provides for easy access to replace the battery and light when necessary.

A spring 34 provides an electrical connection between the anode of the battery and the light. The spring also provides a snug fit between the cathode of the battery and the removable cap 32.

A light switch 36 comprises a button 38 and a resilient metal strip 40. Slight pressure on the button presses the metal strip against the cathode of the battery to complete an electrical connection with the light. The metal strip 40 is in contact with the lead 42 that contacts the negative terminal of the light in a manner to be described below. Release of the button 38 breaks the connection, since the strip 40 is biased to return to the non-contacting position. The metal strip 40 is so flexible that very little pressure is required to engage the strip with the cathode of the battery. Thus, by resting the little finger against the switch 36 the connection is completed.

As previously mentioned the extension tube is hollow in order to form a light channel to direct the light to the lens. The lens holder, of course, also must have some provision to allow the thusly channelled light to pass through to the lens. Accordingly, the lens holder contains a hole 44 at its center. This hole is covered with a plastic window 46 in order to isolate the lens holder from the inside of the apparatus.

An advantage of the lens holder is that it obviates the finger balancing act that must be performed by those not using any insertion device. Furthermore, some of the prior insertion devices rely upon gravity to hold the lens on top of a vertically positioned member. This type of device is not suitable for persons having difficulty controlling their head. A shaky head may knock the lens from the apparatus or knock the entire apparatus over. Also it may be difficult for such an individual to properly align his eye above the apparatus even though the light makes the individual fully aware of the location of the lens. As explained above, other insertion devices have used suction to maintain the lens in position on the holder, but the suction mechanism is generally quite cumbersome and/or complicated.

Another advantage is that the lens does not have to be touched by an operator's fingers since pressing the holder against the convex surface of a lens securely positions the lens against the holder. Thus the lens may be picked up by the holder and washed or disinfected before insertion onto the eye without the lens ever coming into contact with a finger or hand.

The lens holder achieves these and other advantages by providing a partially concave upper surface 48 and a lower surface 50. The upper surface conforms to the shape of a lens to form an air seal when a lens is pressed thereinto. A partial vacuum is created between the lens and the upper surface of the holder since pressing the lens into the holder forces air from between the two elements. This provides a suction that is sufficient to maintain the lens in position when the applicator is raised and turned to any position.

The lens holder 16 (FIG. 1) must be constructed of flexible material that is soft enough to accept and hold a lens without damaging it. Rubber is a suitable material for this purpose.

The hole 44, which is sealed with a transparent member such as the plastic window 46, allows the light from the light source 22 to pass through the center of the lens. In this way the suction is maintained while light is allowed to pass. In addition, there is no air passage between the lens holder and the interior of the apparatus. Thus the difficulties associated with the prior lens applicators arising from the entry of dirt and unsanitary foreign matter into the device are overcome.

Another of the advantages of the present invention is the inclusion of a means for easily breaking the suction between the lens and lens holder after the lens has been placed on the eye. The combination of the suction and suction breaker provides an insertion device that can securely hold yet easily release the lens for positioning onto the eye. The suction breaking means herein described is very easily operated by one finger while the insertion device is gripped by the operator. This represents a marked improvement over previous insertion devices which either had no provision for releasing the lens or incorporated more complicated "plumbing" mechanisms which could not easily be manipulated by one finger of the hand holding the device. These devices also included the air passageway together with the disadvantages attendant therewith which were described above in detail.

The suction release mechanism functions to partially pull the lens holder away from the lens in order to allow air to enter therebetween thereby breaking the suction. As seen in FIG. 2, a suction release switch 52 is connected via a string 54 to the lower surface 50 of the lens holder 16. Although a nylon string is preferable, the string properly may comprise any number of materials. For example, thin wire or strong thread may be employed successfully.

A spring 56 is positioned between the lens holder and a spring stop 58. The spring should be positioned on one side of the lens holder, and displaced 90° from the suction release switch. This placement insures that the spring will not catch the eyelash of the operator. The spring 56 is positioned between the lens holder and a spring stop 58. The spring 54 runs through the center of the spring to connect with the lens holder. The spring biases the lens holder to return to its normal position and keep the string taut. A tube 60 extends between the spring stop 58 and a drip guard 62. The string is fed through this tube. As shown more clearly in FIG. 1, the string is attached to one end of the suction release switch 52. When the switch 52 is depressed the string is tightened which distends the shape of the lens holder 16 to break the vacuum and compress the spring. Upon release of the switch the spring 56 promptly returns the lens holder to its original position.

Actuation of the suction release switch 52 also extinguishes the light 22. FIG. 1 illustrates a resilient metal strip 64 positioned beneath the switch 52 which biases the switch toward its open position and serves as a contact between the lamp and the lead 42. The location designated by the numeral 66 indicates the point of connection between the resilient metal strip and the lead. When the switch is depressed the metal strip is forced away from the lead 42 which opens the connection to turn off the lamp. Thus, depressing the switch simultaneously breaks the vacuum and extinguishes the lamp. The insertion operation thereby is simplified, since the extinguishment of the light serves as a signal to the operator to assure him that the suction between the lens and lens holder has been broken.

A pair of screws 68 and 70 securely fix the extension tube 14 to the housing by friction fit. By loosening the screws the extension tube can be pulled slightly out of the housing or, contrariwise, pushed slightly further into the housing. This telescoping provides a means of adjusting the tension of the string. Should the string not be sufficiently taut, the extension tube can be moved outwardly from the housing, thereby tightening the string. Contrariwise, should the string be too tight, the extension tube can be moved slightly into the housing to reduce the tension in the string.

The insertion apparatus is designed to be easily manipulated by anyone, including persons with severly impaired eyesight. The size of the apparatus together with the positioning of the various elements thereon facilitates the convenient operation of same with only one hand.

The handle portion 28 of the housing 12 contains grooves 72 to facilitate gripping the apparatus. Manipulating the apparatus is further facilitated by a thumb holder 74, which has a concave shape in order to admit part of a thumb. The thumb holder is positioned on the housing opposite the suction release switch by a screw 76. This feature facilitates the grasping of the housing by the user and insures that the fingers of the user can easily operate the light switch 36 and the suction release switch 52. Thus by picking up the applicator and positioning the thumb in the thumb holder the user's fingers are automatically positioned adjacent to the operating switches of the apparatus, as seen in FIG. 3.

A drip guard 62, seen best in FIG. 3, is attached to the extension tube 14. The guard encircles the extension tube 14 and abuts the inner wall of the sleeve 20 in order to prevent liquid from running onto the housing. Thus a lens securely held in place on the lens holder may be immersed in ophthalmic fluid, water, or other liquid for cleaning or disinfecting prior to insertion on the eye. The holder may be immediately rotated and yet the fluid will neither run over or into the housing nor flow onto the fingers of the operator. It is effectively blocked by the drip guard.

The sleeve 20 can be slipped over the extension tube 14 to make a friction fit with the neck portion 30 of the housing 12. As mentioned, the drip guard 62 also tightly contacts the inside surface of the sleeve 20. Thus any accumulation of liquid will be contained within the sleeve and will not drip off onto the operator when the apparatus is tilted to invert the lens.

Another advantage of the apparatus is that it includes means for steadying the device against the cheekbone of the operator and for holding the lower eyelid open during the insertion process. This means comprises the eyelid opener 18 which can be seen in FIGS. 1 and 2. The eyelid opener may be a U-shaped member swivally mounted to either the extension tube 14, the housing 12 or, as shown, the sleeve 20. The eyelid opener pulls the lower eyelid downwardly and also serves as a pivot upon which the applicator may be rotated to bring the lens closer to the eyeball as shown in FIG. 3. Once in place, the operator can look toward the device to see the light. When he sees the light, the contact lens is in the proper position to be inserted. The swivel mount enables the apparatus to be pushed directly toward the eye to insert the lens once it has been properly aligned with the eye. FIG. 1 illustrates that the eyelid opener can swivel up to 20° to facilitate the insertion operation by pivoting from the position shown in solid line to the position shown in dotted line.

In operation a contact lens is pressed into the lens holder 14. This may be done without touching the lens. Pressing the lens into the holder evacuates the air between the lens and the holder and creates a vacuum therein. The vacuum holds the lens in place upon the holder. The user places his thumb within the thumb holder and grasps the housing as shown in phantom in FIG. 3. The natural placement of the fingers, the little finger at the light switch and the large finger at the release switch, allows the light switch 36 to be actuated thereby turning the light on. Since the switch is so sensitive, a slight touch with the little finger turns on the light. The eyelid opener is pressed immediately below the lower eyelid and moved slightly downwardly to open the eye. Using the eyelid opener as a pivot arm, the insertion device is swung up to place the lens close to the eye. The operator then looks toward the light and pushes the device straight towards the eye to place the lens onto his cornea. Once the lens is pressed against the eye the switch 52 is actuated to distend the lens holder 16. The distension allows air to enter between the lens and lens holder breaking the vacuum. At the same time as the release switch 52 breaks the vacuum, it also turns off the light to indicate to the operator that the suction has been broken. Thus the operator can then retract the apparatus.

What is claimed is:

1. An apparatus facilitating the insertion of contact lenses comprising:
   (a) a housing;
   (b) a lens holder extension tube attached to said housing and supported thereby for providing a light channel;
   (c) a flexible concave lens holder attached to and supported by said lens holder extension tube for holding a contact lens to be inserted by forming a partial vacuum between said lens and said lens holder, said lens holder including means at its center communicating with the light channel provided by said lens holder extension tube for allowing light to pass therethrough and thereby assist the operator in guiding a lens;
   (d) illuminating means contained within said housing and positioned at the end of said extension tube for providing illumination to said lens holder;
   (e) a power source for powering said illuminating means;
   (f) an eyelid opener swivelly connected to and extending from said housing for opening the lower eyelid of the eye, for steadying the apparatus against the cheekbone of the user, and for guiding the lens into the proper position on the eye;
   (g) a suction breaker operationally connected to said lens holder for allowing air to enter between said lens and said lens holder in order to break the suction therebetween and thereby easily remove the apparatus from the lens once the lens has been positioned on the eye;
   (h) a suction breaker switch positioned on said housing for activating said suction breaker and for turning off said illuminating means;
   (i) a light switch operationally connected to said illuminating means and positioned at the end of said housing opposite said lens holder for activating said illuminating means; and
   (j) a thumb holder attached to said housing in a position approximately 180° displaced from said suction breaker switch for facilitating the gripping of said apparatus by an individual and for facilitating the proper alignment of the individual's fingers upon said apparatus for easy operation thereof.

2. An apparatus as in claim 1 wherein said eyelid opener comprises a U-shaped wire swivelly connected to said housing, said wire being movable from a first position for serving as a pivot arm for rotating said apparatus, to a second position for allowing the lens to be pushed directly onto the eye of an operator.

3. An apparatus as in claim 1 wherein said suction breaker comprises a string attached to the perimeter of the back-side of said flexible lens holder and a spring encircling part of said string, said spring being positioned between said lens holder and a spring stop, whereby tension on said string partially deforms the shape of said lens holder in order to allow air to enter the space between said lens holder and said lens.

4. An apparatus as in claim 1 further comprising a removable sleeve partially encircling said extension tube, said eyelid opener being pivotly mounted to said sleeve and movable from a first position for serving as a pivot arm for rotating said apparatus to guide the lens close to the eye of an operator, to a second position for allowing the lens to be pushed directly onto the eye of said operator.

5. An apparatus as in claim 1 further comprising a drip guard positioned on said extension tube between said lens holder and said housing for preventing the flow of liquid on or into said housing or onto the fingers of an operator.

* * * * *